United States Patent [19]

Halpern et al.

[11] Patent Number: 4,810,586

[45] Date of Patent: * Mar. 7, 1989

[54] METHOD ENHANCED POLYSACCHARIDE COATING OF PLASTIC OBJECTS

[76] Inventors: Gregory Halpern, Wilson Park Dr., Tarrytown, N.Y. 10591; Jack U. Gould, 500 E. 58th St., New York, N.Y. 10028

[ * ] Notice: The portion of the term of this patent subsequent to Apr. 14, 2004 has been disclaimed.

[21] Appl. No.: 136,804

[22] Filed: Dec. 22, 1987

Related U.S. Application Data

[62] Division of Ser. No. 932,237, Nov. 19, 1986, abandoned, which is a division of Ser. No. 852,602, Apr. 16, 1986, Pat. No. 4,657,820.

[51] Int. Cl.$^4$ .............................................. B32B 9/02
[52] U.S. Cl. ............................... 428/476.6; 106/157; 106/162; 536/1.1
[58] Field of Search ............................. 106/157, 162; 428/476.6; 536/1.1

[56] References Cited

U.S. PATENT DOCUMENTS

| | | | |
|---|---|---|---|
| 2,137,006 | 11/1938 | Schrauth | 106/157 |
| 3,447,940 | 6/1969 | Halleck | 106/162 |
| 4,139,395 | 2/1979 | Dunlap | 106/157 |
| 4,154,857 | 5/1979 | Higgins | 106/157 |

OTHER PUBLICATIONS

93:127469k, An Interaction of Albumin with Hyaluronic Acid Chondroitin Sulfate, Gold, E., Biopolymers, 1980, 19(7), 1407–14 (Eng).

*Primary Examiner*—Paul Lieberman
*Assistant Examiner*—Willie J. Thompson
*Attorney, Agent, or Firm*—David H. Semmes

[57] ABSTRACT

Hydrophilic coating of plastics, particularly an enhanced aqueous solution of a polysaccharide which flows uniformly over the surface of an anchor film applied to the plastic. The aqueous solution of a polysaccharide from the group consisting of hyaluronic acid and its salts, chondroitin sulfate and agarose is enhanced by the addition of albumin to provide uniform wetting over the anchor film on the plastic.

8 Claims, No Drawings

METHOD ENHANCED POLYSACCHARIDE COATING OF PLASTIC OBJECTS

CROSS-REFERENCE TO RELATED APPLICATIONS

A division of applicant's Enhanced Polysaccharide solution, Ser. No. 932,237, filed 11/19/1986, now abandoned, in turn, a division of applicant's Enhanced Polysaccharide solution, Ser. No. 852,602, filed 4/16/86, now U.S. Pat. No. 4,657,820.

The present application is directed to enhancing the aqueous solution of a polysaccharide, such as hyaluronic acid and its salts, chondroitin sulfate, agarose and the like. The enhanced solution provides uniform wetting over the surface of an anchor film applied to plastics.

BACKGROUND OF THE INVENTION (1) Field of the Invention:

Hydrophilic coating of plastics, particularly a polysaccharide solution which is enhanced by the addition of albumin to provide improved wetting characteristics.

(2) Description of the Prior Art:

Being separately submitted.

SUMMARY OF THE INVENTION

According to the present invention, aqueous solutions of polysaccharides from the group comprising hyaluronic acid and its salts, chondroitin sulfate, agarose and the like, are enhanced by the addition of albumin to thoroughly wet the hydrophobic surface of a plastic, as well as an anchor film which may be applied to the plastic.

DESCRIPTION OF THE PREFERRED EMBODIMENTS

Aqueous solutions of polysaccharides such as hyaluronic acid and its salts, chondroitin sulfate, agarose, and the like, are well-known for their viscous, slippery, lubricious nature which is responsible for their utility in the body of man and other animals.

Various inventors have incorporated polysaccharides into compositions intended for use as body implants or prostheses, for the purpose of improving comfort of the wearer. Such compositions are heterogeneous, polyphasic and opaque, because the polysaccharides are basically insoluble and incompatible with the load-bearing components of a part such as an implant or prosthesis. Such discontinuous dispersions may nevertheless be of value for a limited period of time, as the polysaccharide is leached to the surface of the part by aqueous body fluids and there acts to lubricate the surface until it is carried away by body fluids. Eventually, of course, the reservoir of polysaccharide is depleted, and its beneficial effect on comfortable operation of the part is no longer exerted.

In some cases, inventors of such compositions have provided crosslinking of the polysaccharide, so that it is not leached away and lost. In those cases, however, it is obvious that the insolubilized polysaccharide in reserve deposits below the surface of the part can no longer be leached to the surface and might better not be present at all. Thus, the crosslinking polysaccharide that happens to be at the surface of the part is not providing a continuous, lubricating film, but on the contrary acts relatively inefficiently, as small slippery spots here and there on the surface of the part.

As described in the aforementioned copending application, applicants have grafted continuous insolubilized films of polysaccharides onto the surface of rigid materials, such as plastics and metals, so that formed parts are endowed with excellent lubrication when wet. Furthermore, since the continuous surface coating is grafted and crosslinked, the lubricating effect is permanent and cannot be washed away. Still further, when the underlying plastic body is transparent, the continuous surface coating is also transparent and of excellent optical quality, so that lubricious contact lenses and intraocular lenses can be fabricated in this manner without harmful effects on the optical quality of the device.

According to application Ser. No. 643,598, the most useful procedure for preparing such coated objects is first to apply an anchor coat on the formed object of interest. This anchor coat will be of such composition as to adhere strongly to the underlying body, with the appropriate degree of flexiblity to tolerate bending and twisting without failure, and to provide reactive groups which will allow for chemical grafting to the polysaccharide coat later applied. Such anchor coats may, for example, be acrylic copolymers containing a multitude of hydroxyl, carboxyl, epoxy, amino, or other functional groups for later reaction with appropriate grafting agents.

However, when one attempts to prepare such articles, he encounters in many cases certain natural obstacles that operate against and prevent realization of the desired uniform coating. The first barrier is the peculiar solubility of hyaluronic acid, of its salts, and or most other polysaccharides of interest; i.e., the choice of solvents is limited almost exclusively to water. With aqueous solutions of sodium or potassium hyaluronate, viscosities are appropriate for conventional coating processes when the solute concentration is in the range of 0.5 to 1.5%. The corresponding viscosity is obtained with chondroitin sulfate at a concentration of 5 to 20% in water.

When such solutions are applied to the surface of the anchor coat, the second barrier is encountered: the aqueous solution does not wet the hydrophobic surface, and the solution crawls into strings and isolated droplets and pools. A useful, fully continuous, transparent film does not form.

Applicants add small amounts of purified albumin, from about 0.1% to several percent by weight of the polysaccharide, and so cause the aqueous solution to flow uniformly over the surface of the anchor film, when applied by conventional coating techniques, to produce useful, continuous, transparent coatings or films. With appropriate grafting reagents, these coatings or films can be anchored to the underlying anchor coat and become permanent hydrophilic surfaces of great utility.

The albumin may be derived from any of a wide variety of plant and animal tissues and fluids, but perhaps most often from the blood serum of animals. The isolation and purification procedures used in isolating the albumin from other proteins and lipids will determine the degree of purity of the albumin produced, even to the extent that pure, crystalline product can be obtained. According to the present invention, most conventional grades of albumin are effective in achieving the flow and film uniformity desired in this invention. However, other considerations may determine the degree of purity to be preferred. For example, in the case of implanting a coated medical device in the human body, it may be prudent to use a grade of albumin that will not cause undesired immunological reactions. Methods of isolating and purifying albumins have been detailed in the chemical literature (e.g., E. J. Cohn, et al., J. Am. Chem. Soc., Vol. 68, pp. 459–475, 1968; ibid., Vol. 69, pp. 1753-1761, 1969; R. F. Chen, J. Biol. Chem., Vol. 242, pp. 173-180, 1967).

The following examples are intended to illustrate, but not to limit the invention.

EXAMPLE 1

A solution acrylic polyer comprising 7.5 mole-percent hydroxyethyl methacrylate was applied at a wet thickness of approximately 3 mils to the clean surface of a panel of polymethyl methacrylate. It was dried at a temperature of 65 degrees Centigrade and at 20 inches of vacuum, for 25 minutes. When the panel had cooled to room temperature, an 0.5% aqueous solution of "ultra-pure" sodium hyaluronate (MedChem Products, Inc.) was applied as a second coat intended to have 3 mils wet thickness also. However, immediately after application, the wet film crawled and gathered into strings and droplets scattered over the anchor coat. When the film applicator was drawn over this surface a second time, the dispersed solution was pulled together again to some degree, but it quickly crawled again and was unable to form a continous coating. When placed in the oven at 65 degrees and 20 inches of vacuum for two hours, the final panel showed a webbed pattern corresponding to the conformation of the wet surface. The surface was not optically uniform, and the ability of the surface to shed water appeared to be the same as that of a panel coated only with the anchor coat.

EXAMPLE 2

Nine Plexiglas panels were coated with the same acrylic anchor coat as in Example 1 and cured in the same manner. Onto one was then applied 3 mils of the same hyaluronate solution as that described in Example 1, and onto the other eight was applied the same hyaluronate solution containing one of the following levels of bovine albumin (crystallized and lyophilized, essentially free of fatty acids): 0.5%, 0.1%, 0.25%, 0.5%, 1.5%, 5%, 10%, and 25%. The top coats containing 0% and 0.05% albumin crawled and gathered into strings and droplets; all other panels had continous coatings with optical clarity and uniformity.

EXAMPLE 3

Example 2 was repeated in every respect, except that the polysaccharide was chondroitin sulfate (7.5% solution in water). Again, the top coats containing 0% and 0.05% (w/w on chondroitin sulfate) of albumin crawled and gathered, but those containing higher levels of albumin were smooth and uniform both before and after curing.

EXAMPLE 4

Two Plexiglas panels coated with the anchor coat and dried as in Example 1, were coated with 1% aqueous solutions of potassium hyaluronate isolated from submerged culture in "pure" form. The nominal 6-mil top-coat or film on the first panel (contaning 0.% albumin) crawled and gathered and produced a non-uniform coating of no value.

In the second panel, the aqueous solution applied as a top-coat contained 0.5% (w/w on hyaluronate) of the bovine albumin described in Example 1; the applied top-coat did not crawl, but formed a smooth, uniform, clear and transparent film with good lubricity and non-beading behavior when wetted.

EXAMPLE 5

Portions of 1% aqueous solution of potassium hyaluronate from human umbilical cord (Sigma Chemical Company Grade III-P) were treated with 0.5%, 1.0% and 5% (w/w on hyaluronate) of chicken egg albumin (crystallized and lyophilized; essentially salt-free: Sigma Chemical Company Grade VI). All mixtures produced smooth, uniform top-coats when knifed over the anchor coat described in Example 1.

EXAMPLE 6

An aqueous solution was prepared containing 0.5% of "pure" sodium hyaluronate (MedChem Products, Inc.) and 0.5% (w/w on hyaluronate) of human albumin (crystallized and lyophilized; essentially globulin-free. When this solution was knifed onto the anchor coat described in Example 1 at a setting of 10 mils, a smooth, uniform, colorless, clear film was obtained both before and after curing.

We claim:
1. Method comprising:
  (a) coating a plastic object with an acrylic polymer solution permitted to dry as an anchor coat; and
  (b) sequentially applying an aqueous solution as a top coat to said anchor coat, said aqueous solution including:
    i. a polysaccharide from the group consisting of hyaluronic acid and its salts, chondroitin sulfate and agarose; and
    ii. 0.25 to 25% albumin, w/w on the polysaccharide.
2. Method of enhanced polysaccharide coating of a plastic object as in claim 1, wherein said polysaccharide is sodium hyaluronate 0.1 to 25%.
3. Method of enhanced polysaccharide coating of a plastic object as in claim 1, wherein said albumin is bovine albumin, crystallized and lyophilized, essentially free of fatty acids.
4. Method of enhanced polysaccharide coating of a plastic object as in claim 1, wherein said polysaccharide is chondroitin sulfate, at least 0.05%.
5. Method of enhanced polysaccharide coating of a plastic object as in claim 1, wherein the polysaccharide is sodium hyaluronate, isolated from submerged culture in "pure" form.
6. Method of enhanced polysaccharide coating of a plastic object as in claim 1, wherein:
  a. said aqueous solution contains 1% aqueous potassium hyaluronate obtained from human umbilical cord; and
  b. said albumin is chicken egg albumin 0.5 to 5% w/w on said hyaluronate, crystallized and lyophilized; essentially salt free.
7. Method of enhanced polysaccharide coating of a plastic object as in claim 1, wherein said aqueous solution contains at least 0.5% pure sodium hyaluronate and said albumin is in the form of human albumin crystallized, and lyophilized; essentially globulin free.
8. Method of enhanced polysaccharide coating of a plastic object as in claim 1, wherein:
  a. said aqueous solution contains 1% aqueous sodium hyaluronate obtained from human umbilical cord, and
  b. said albumin is chicken egg albumin 0.5 to 5% w/w on said hyaluronate, crystallized and lyophilized; essentially salt free.

* * * * *